United States Patent
Oguchi

(10) Patent No.: US 8,404,441 B2
(45) Date of Patent: Mar. 26, 2013

(54) DNA INTERCALATOR DETECTION

(75) Inventor: Shinobu Oguchi, Tokyo (JP)

(73) Assignee: Empire Technology Development LLC, Wilmington, DE (US)

( * ) Notice: Subject to any disclaimer, the term of this patent is extended or adjusted under 35 U.S.C. 154(b) by 204 days.

(21) Appl. No.: 12/762,474

(22) Filed: Apr. 19, 2010

(65) Prior Publication Data

US 2011/0257026 A1 Oct. 20, 2011

(51) Int. Cl.
*C12Q 1/68* (2006.01)
(52) U.S. Cl. .......................................... 435/6.1
(58) Field of Classification Search ................... None
See application file for complete search history.

(56) References Cited

U.S. PATENT DOCUMENTS

| | | | | |
|---|---|---|---|---|
| 4,880,731 | A * | 11/1989 | Kaspar | 435/7.94 |
| 2003/0092055 | A1 | 5/2003 | Yun et al. | |
| 2004/0072158 | A1* | 4/2004 | Henkens et al. | 435/6 |
| 2004/0086423 | A1* | 5/2004 | Wohlstadter et al. | 422/52 |
| 2005/0065335 | A1 | 3/2005 | Lyles | |
| 2006/0252067 | A1 | 11/2006 | Hongo et al. | |
| 2007/0148675 | A1* | 6/2007 | Zhang et al. | 435/6 |

FOREIGN PATENT DOCUMENTS

| | | |
|---|---|---|
| JP | 09-288080 | 11/1997 |
| JP | 2000-125865 | 5/2000 |
| JP | 2002-171996 | 6/2002 |
| JP | 2002-320476 | 11/2002 |
| JP | 2003-090818 | 3/2003 |
| JP | 2008-200594 | 9/2008 |
| WO | 2004/091753 A1 | 10/2004 |
| WO | 2005/123249 A1 | 12/2005 |

OTHER PUBLICATIONS

Marrazza et al, Analytica Chimica Act, vol. 387, pp. 297-307 (1999).*
M. Mascini "Affinity electrochemical biosensors for pollution control" Pure Appl. Chem., vol. 73, No. 1, pp. 23-30, 2001.
International Search Report and Written Opinion, mailed Aug. 9, 2010, as issued in connection with corresponding Patent Application No. PCT/US2010/036609, filed on May 28, 2010.
Ministry of the Environment, Government of Japan "Air and water pollution by dioxins, water pollution (including contamination of bottom sediment.) Soil Pollution and Environmental Quality Standards" Environment Agency Notification No. 68 of Dec. 27, 1999 [Online: http://www.env.go.jp/kijun/dioxin.html].
Kazuhiro Kuwata "Determination of chrysene and benzopyrene in the atmospheric environment by mass spectrometry" Japan analyst 27(10), 650-655, 19781005.
Shimadzu Good Laboratory Component Ltd. [Online: https://solutions.shimadzu.co.jp/glc/catalog/pdf/391-393.pdf] GC/LC Catalog.

(Continued)

*Primary Examiner* — Robert T. Crow
(74) *Attorney, Agent, or Firm* — Maschoff Brennan

(57) ABSTRACT

A DNA intercalator detection system can include a filtration unit a control sample conditioner operably coupled with the filtration unit and an analytic unit operably coupled with the filtration unit and control sample conditioner and having an electronic chemical array (ECA) reaction component. A data processing unit is operably coupled with the analytic unit and configured to compare and determine a difference between electronic data of a test sample and a conditioned control sample from the ECA reaction component. The difference provides an indication of whether or not a DNA intercalator is present in the test sample.

10 Claims, 8 Drawing Sheets

OTHER PUBLICATIONS

Agilent Technologies, Inc. "Agilent's new octadecylsilane (ODS) (C18) solid-phase extraction cartridge: C18 Sanpuriku" Printed in Japan Aug. 11, 2008 5989-9326JAJP [Online: http://www.chem-agilent.com/cimg/low_5989-9326JAJP.pdf].

Japanese Patent Office, Technology Trends Group Patent Policy Planning Division General Affairs Department "Collection for Standards and Technology—Nucleic acid amplification and detection—section 5-2-2-1 DNA microarray" Mar. 14, 2007 [Online: http://www.jpo.go.jp/shiryou/s_sonota/hyoujun_gijutsu/kakusan/0072.html].

Yoshio Isimori "DNA Chips" Journal of Surface Science Society of Japan, vol. 24, No. 11 pp. 671-676, 2003 [Online: http://www-surface.phys.s.u-tokyo.ac.jp/sssj/Vol24/24-11/11g671-676.pdf].

Masahiko Amano "Case Study: ECA Chip—Biochip in the Next Generation" Nature Interface Jun. 2003, No. 15, 034.

Hukushima Atsushi "Preparation and analysis of DNA fluorescence by ultraviolet irratiat of the film" [Online: http://www.plantatree.gr.jp/scholarship/H14-fukushima02.html] 2004.

Hukushima Atsushi, et al "The functional polymers prepared from salmon milt discarded Environmental Disaster Sex-integrated—Salmon milt DNA by UV and fluorescence analysis of the film prepared" [Online: http://wwwsoc.nii.ac.jp/jsac/63touron/06.html].

Dianne M. Ferry, et al "Sensitive liquid chromatographic assay for the basic DNA intercalator" Journal of Chromatography B, 763 (2001) 149-156.

Koji Hashimoto, et al "Preliminary evaluation of electrochemical PNA array for detection of single base mismatch mutations" Lab on a chip 1: 61-63, 2001.

Koji Hashimoto, et al "Microfabricated disposable DNA sensor for detection of hepatitis B virus DNA" Sensors and Actuators B 46: 220-225, 1998.

\* cited by examiner

DNA INTERCALATOR DETECTION

BACKGROUND

DNA intercalators contain many chemical substances that have a harmful effect on human health. Typical examples of these substances include carcinogens and endocrine disruptors, which have a polycyclic aromatic molecular structure. For instance, testing systems have been developed to monitor benzopyrene and dioxins, which are typical DNA intercalators. In one system, samples collected in the environment (e.g., atmosphere, river, and soil) are taken to a laboratory and subjected to a robust chemical analysis. In another system, gene expression profiles for cells sensitive to DNA intercalators are detected in a laboratory setting. There is an interest for the creation of new risk-screening systems in which the level of a DNA intercalator in the environment can be checked on site easily and quickly in advance of implementing laboratory testing.

SUMMARY

In one aspect, a DNA intercalator detection system can include a filtration unit; a control sample conditioner unit configured to receive a portion of a filtered sample from the filtration unit and remove a DNA intercalator from the sample so as to produce a conditioned control sample; an analytic unit configured to receive a portion of the filtered sample from the filtration unit (e.g., test sample) and to receive the conditioned control sample from the control sample conditioner unit, wherein the analytic unit has one or more electronic chemical arrays (ECAs); and a data processing unit configured to compare and determine a difference between electronic current of the filtered sample and the conditioned control sample from the one or more ECAs. The difference provides an indication of whether or not a DNA intercalator is present in the filtered sample.

In one aspect, a method for detecting a DNA intercalator in an environmental sample can include filtering an environmental sample to obtain a filtered sample; splitting the filtered sample into two or more separate portions; conditioning one or more portions of the filtered sample such that one or more DNA intercalators are removed therefrom to form a conditioned control sample; contacting a portion of the filtered sample with double stranded nucleic acids having a strand linked to an ECA, wherein the portion of the filtered sample contacted with the double stranded nucleic acids is a test sample; contacting the conditioned control sample with double stranded nucleic acids having a strand linked to an ECA; obtaining electronic data from an electronic current of the test sample and from an electronic current of the conditioned control sample; and determining a difference between the electronic data from the test sample and the conditioned control sample. The difference provides an indication of whether or not a DNA intercalator is present in the sample.

In one aspect, a method for detecting a DNA intercalator in an environmental sample can include introducing the environmental sample into a portable DNA intercalator detection system at the location, wherein the DNA intercalator detection system can include a filtration unit, a control sample conditioner unit, an analytic unit, and a data processing unit; filtering the environmental sample with the filtration unit so as to remove environmental substances from the environmental sample and provide a filtered sample; conditioning a portion of the filtered sample with the control sample conditioner unit so as to remove one or more DNA intercalators and form a conditioned control sample; contacting, in the analytic unit, the test sample and conditioned control sample with double stranded nucleic acids having a strand linked to an ECA; obtaining electronic data from an electronic current of the test sample and the conditioned control sample when in contact with the double stranded nucleic acids; and determining a difference between the electronic data from the test sample and the conditioned control sample with the data processing unit. The difference provides an indication of whether or not a DNA intercalator is present in the sample.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
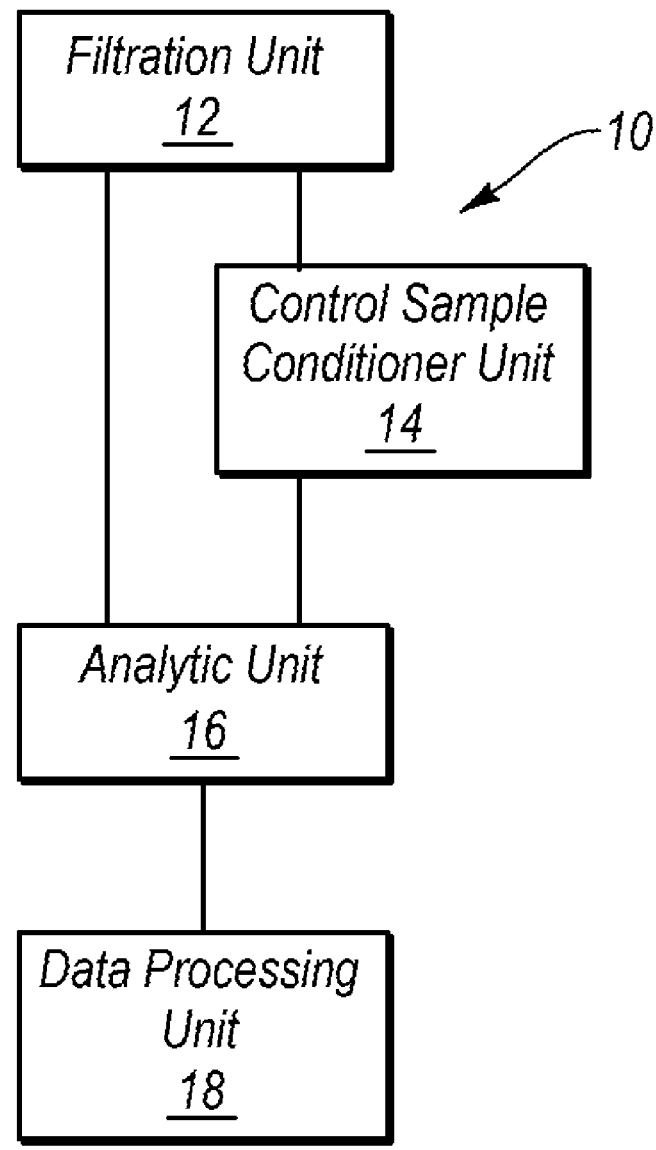
FIG. 1 is an illustrative example of a DNA intercalator testing system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

A testing system can be used in testing various environmental compositions (e.g., water) for the presence or levels of DNA intercalators, such as benzo[a]pyrene and dibenzo-p-dioxin as well as other intercalators. DNA intercalators intercalate or reversibly bind with double stranded DNA. Intercalation occurs when molecules of an appropriate size and chemical nature fit between base pairs of DNA. DNA intercalators are known to be a health risk and identification of the presence and/or determining the amount or concentration of DNA intercalators in the environment can be important. The testing system can have various components that can process a sample for testing, which components are described in more detail below. The testing system can be installed in a laboratory or configured to be portable.

The DNA intercalators can be hydrophobic DNA intercalators, such as but not limited to DNA intercalators having one or more aromatic rings, polyaromatics, heterocyclic aromatics, and combinations thereof, such as polycyclic aromatic hydrocarbons. The flat portions of these types of substances intercalate between base pairs of DNA. Non-limiting examples of hydrophobic DNA intercalators includes carbazoles, acridines, anthracenes, anthracyclines, ethidium bromides, proflavines, daunomycins, doxorubicins, thalidomides, quinacrines, derivatives thereof, and combinations thereof.

In one option, the testing system is portable. As such, the testing system can be delivered to a testing site or environmental location. Examples of portability can include the testing system having a size that one or more persons can move the testing system, and may include a deck having the components of the system. The portable system can also include wheels for moving and transportation of the system. In light of the rising public concern over environmental and health issues, the testing system can quickly be taken to a test site to test for the presence or amounts of DNA intercalators. As such, the portable testing system can be contained within a vehicle, on trailer, or the like for transportation. The portable testing system can then perform an onsite analysis of the environment for risk-screening for DNA intercalators. This portable testing system has advantages over conventional equipment and methods which require samples to be transported to a specific laboratory for a robust chemical analysis by a professional technician.

In one embodiment, the testing system can be configured to perform a rough study or general analysis for the presence or amount of one or more potential DNA intercalators. After the rough study, a positive result can then qualify the sample as being suitable a robust chemical analysis for an in-depth analysis of the DNA intercalator. On the other hand, the testing system can be configured to identify the presence or amount accurately enough to be a standalone system and analytical process.

The DNA intercalator detection system can include one or more of a filtration unit, a control sample conditioner unit, an analytic unit, and a data processing unit. The control sample conditioner unit can be configured to receive a portion of a filtered sample from the filtration unit. The analytic unit can be configured to receive a portion of the filtered sample from the filtration unit and a conditioned control sample from the control sample conditioner unit. Also, the analytic unit can have one or more electronic chemical arrays (ECAs). For example, the analytic unit can have one ECA for the filtered sample and one ECA for the conditioned control sample. Alternatively, a single ECA can be used to analyze the filtered sample and the conditioned control sample. The data processing unit can be configured to receive electronic data from the analytic unit, and can be configured to compare and determine a difference between electronic data of the filtered sample (e.g., a test sample) and the conditioned control sample. The difference in electronic data between the filtered sample and the conditioned control sample can provide an indication of whether or not a DNA intercalator is present in the test sample.

The filtration unit can be configured to filter components from a sample. The filtration unit can include a filter that can be configured as any type of filter that can allow certain components of a sample to pass through the filter while trapping or retaining certain components from the sample. The filtration unit can include a filter that can separate environmental and/or biological materials from an environmental sample. In an embodiment for filtering water samples, the filter can be a membrane filter having a hydrophilic property. Alternatively, the filter can include a hydrophobic property. Examples of filters can include without limitation mixed cellulose esters (MCE), glass filter materials, nylon, cellulose acetate, polyvinylidene difluoride (PVDF), polytetrafluoroethylene (PTFE), or polycarbonate.

In one embodiment, the testing system can include a sample divider configured to receive a filtered sample from the filtration unit and then to split the filtered sample into two or more separate compositions. One of the compositions can be a test sample and one or more of the separate compositions being the control sample that is processed into a conditioned control sample as described herein.

The control sample conditioner unit can include a hydrophobic component configured to attract and retain hydrophobic DNA intercalators from the control sample. The control sample conditioner unit can be configured as a separation column (e.g., FPLC, HPLC) or other separation unit that has a hydrophobic component that can attract hydrophobic DNA intercalators from the sample by hydrophobic interaction. For example, the hydrophobic component can include without limitation C8 to C20 hydrocarbons that are linear, cyclic, or branched, substituted or unsubstituted, aromatic or non-aromatic, carbon homo atoms or hetero atoms, such as phenyl components and octadecylsilyl-based components such as but not limited to octadecylsilyl-silica gels, octadecylsilyl columns, and octadecylsilyl matrices, and/or hydrocarbon components such as but not limited to polymethacrylates having butyl, ether, or phenyl ligand.

The analytic unit is configured to receive samples and analyze the samples for the presence of a hydrophobic DNA intercalator. Accordingly, the analytic unit includes sample receiving components and sample analyzing components, which are described in more detail below. The analytic unit can include any one or more components or configurations, some of which include: a port fluidly coupled with the sample divider and configured to receive the test sample; a port fluidly coupled with the control sample conditioner unit and configured to receive the conditioned control sample; one or more sample chambers configured to receive one or more samples; one or more fluid pathways configured to deliver the test sample and conditioned control sample to the one or more sample chambers; an integrated or removable ECA reaction component having: a working electrode, counter electrode, and/or reference electrode (e.g., two electrode or three electrode detection system); a nucleic acid strand operably coupled with one of the electrodes such that the electrodes can receive electrons from the nucleic acid; and a complementary nucleic acid strand either hybridized or hybridizable with the electrode-coupled nucleic acid; electronic components configured to measure an electronic current passed from the electrode-coupled nucleic acid; voltammetry electronic components; electronic components configured to obtain electronic data from the electrodes; a transmitter to transmit electronic data to the data processing unit; or a receiver to receive instructions from the data processing unit.

The data processing unit can include hardware and/or software configured to operate components of the system, such as the filtration unit, sample divider unit, control sample conditioner unit, or analytical unit. The data processing unit can also be configured to compare electronic data from the test sample with the conditioned control sample. As such, the data processing unit can include a computer-readable memory device having computer-executable instructions to operate the system and/or analyze data obtained from testing samples with the system. The data processing unit can be configured or programmed to automatically receive data from the analytic unit and/or automatically process the data to determine the presence of a DNA intercalator. Alternatively, the data processing unit can be configured or programmed to receive instructions from a user for the receipt or processing of data from the analytic unit.

The system can include one or more user interfaces, which include a user input interface and an output interface. The user input interface can include common computing devices that allow a user to interface with a computing system. Examples include keyboards, mice, light pens, touch screens, buttons, knobs, switches, or the like. The output interface can include common computing devices that provide information to a user. Examples include monitors, screens, speakers, lights, printers, and the like. Also, the system can be operably coupled with a communication network (e.g., wired, optical, or wireless) so that the data and/or results of the processed data can be transmitted over the communication network.

A method for detecting a DNA intercalator in an environmental sample can include filtering an environmental sample so as to remove environmental substances from the environmental sample and to provide a filtered sample; splitting the filtered sample into two or more separate compositions, one or more of the separate compositions being a test sample and one or more of the separate compositions being a control sample; conditioning the control sample so as to remove one or more DNA intercalators and to form a conditioned control sample; contacting the test sample and conditioned control sample with double stranded nucleic acids each having a strand linked to an ECA; detecting electronic data of the test sample and the conditioned control sample; determining a difference between the electronic data from the test sample and the conditioned control sample. The difference provides an indication of whether or not a DNA intercalator is present in the sample.

The method for detecting a DNA intercalator in an environmental sample can also include any one or more of the following: collecting the environmental sample from a location and performing the method at the location; removing, with a filtration unit, biological materials from the environmental sample; contacting the control sample to a hydrophobic component capable of attracting and retaining hydrophobic DNA intercalators from the control sample; measuring the electronic currents of the test sample and conditioned control sample; hybridizing a nucleic acid strand coupled to the ECA with its complementary nucleic acid; conducting a voltammetry protocol; transmitting the electronic data to a data processing unit. For example, this can include processing the electronic data in the data processing unit in order to determine a difference between the electronic data from the test sample and the conditioned control sample.

According to another aspect, a method can include determining an amount or health risk of a DNA intercalator or detecting a DNA intercalator in an environmental sample. Such a method can include: collecting an environmental sample from a location; introducing the environmental sample into a DNA intercalator detection system (e.g., portable system) at the location; filtering the environmental sample with the filtration unit so as to remove environmental substances from the environmental sample and provide a filtered sample; conditioning a portion of the filtered sample with the control sample conditioner unit so as to remove one or more DNA intercalators and form a conditioned control sample; contacting, separately in the analytic unit, the test sample and conditioned control sample with double stranded nucleic acids each having a strand linked to a electronic chemical array (ECA); obtaining electronic data from the electronic currents of the test sample and the conditioned control sample when contacted with the nucleic acids; and determining a difference between the electronic data from the test sample and the conditioned control sample with the data processing unit. The difference provides an indication of whether or not a DNA intercalator is present in the sample.

FIG. 1 depicts an illustrative example of a configuration of the DNA intercalator testing system 10, which includes a filtration unit 12, a control sample conditioner unit 14, an analytic unit 16, and a data processing unit 18.

The filtration unit 12 can be configured to filter a sample, which is then provided to the control sample conditioner unit 14. For example, fluid pathways, pipettes, or the like can provide the filtered sample to the control sample conditioner unit 14. Similarly, the filtration unit 12 and control sample conditioner unit 14 can provide samples to the analytic unit 16. The analytic unit 16 can be in communication with the data processing unit 18 so that data can be passed therebetween. For example, the analytic unit 16 can be in communication with the data processing unit 18 by wires, optics, or wireless communication.

Figure 2:
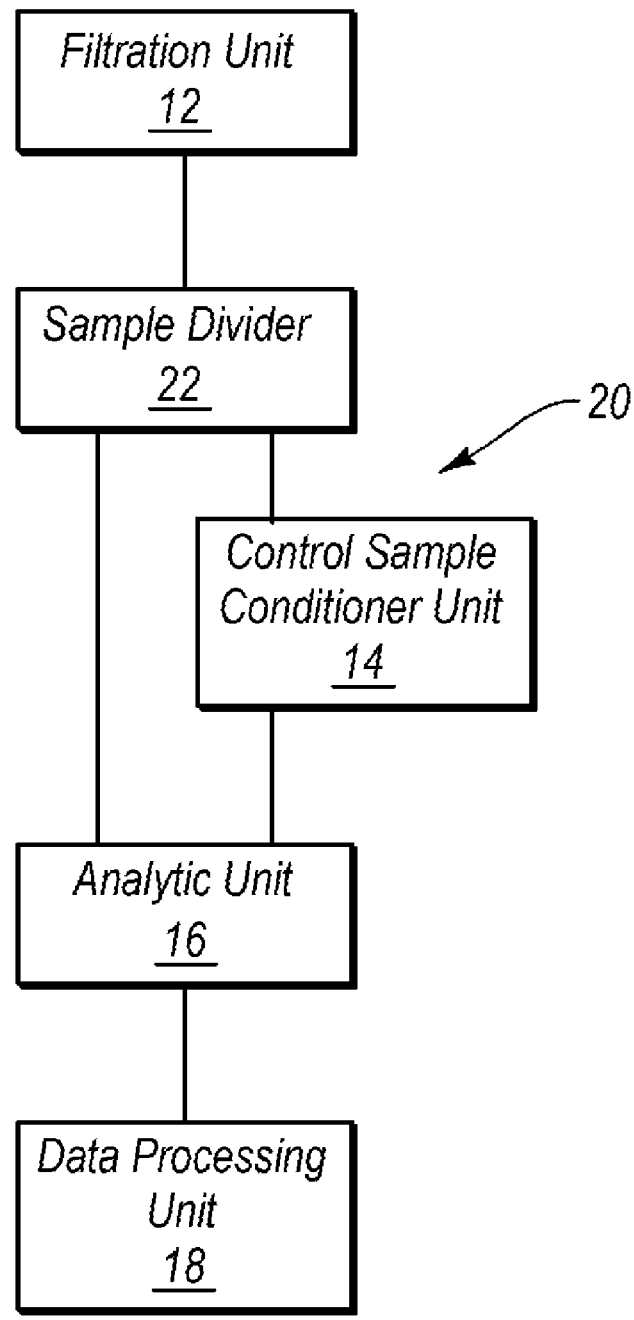
FIG. 2 is an illustrative example of a DNA intercalator testing system.

FIG. 2 depicts another illustrative example of a configuration of the DNA intercalator detection system 20, which includes a filtration unit 12, a sample divider 22, a control sample conditioner unit 14, an analytic unit 16, and a data processing unit 18.

In one embodiment, the testing system 10 or 20 does not include the filtration unit 12 because samples can be obtained that do not need to be filtered. For example, some water samples may not need filtration.

Similar to the embodiment of the DNA intercalator detection system 10 of FIG. 1, the DNA intercalator detection system 20 of FIG. 2 includes the components being operable with each other. As such, the filtration unit 12 can provide a filtered sample to the sample divider 22 by using fluid pathways, pipettes, or the like.

The filtration unit 12 can be configured to receive an environmental sample and to remove environmental substances from the environmental sample and to provide a filtered sample. As such, the filtration unit 12 can receive various types of samples ranging from soil, plant components, animal components, water and the like. The filtration unit 12 can include filter components, such as a filter, tubing, filter housing, or the like (not shown), which are common in filtration units. Filtration units are common devices used to separate materials, and as such any appropriate type of filtration unit can be included in the DNA intercalator detection system 10. The filtration unit 12 can be configured to separate environmental and/or biological materials from an environmental sample by capturing and retaining environmental and/or biological materials from the sample.

In one embodiment, the filtration unit 12 may be configured to remove materials from the environmental sample, such as foreign matter, plankton, microbes, proteins, and the like. The filtration unit 12 can include a filter (not shown), which is configured to allow certain substances in a sample to pass therethrough while trapping and retaining some substances from the sample. The filter can be formed from various materials that are commonly used for filters: such as polymers such as but not limited to polyvinylidene difluoride (PVDF), polyethylene, polypropylene, polytetrafluoroethylene (PTFE), or polycarbonate; metals such as but not limited to stainless steel, aluminum, or galvanized steel; ceramics such as but not limited to aluminum oxides, zirconia, carbides, borides, nitrides, or silicides; or composites such as but not limited to woven wire with fiber metal felt and composite materials formed from polymers, metals, and/or ceramics. For example, the filtration unit 12 can include a filter made from polyvinylidene difluoride (PVDF). Thus, the filtration unit 12 can be configured to remove foreign materials from the environmental sample while leaving the DNA intercalators in the filtered sample so as to improve the effectiveness of the testing system and testing protocols.

The filtration unit 12 can include a removable filter that can be replaced or replenished when the filtering capacity is reduced. In some instances the substances, such as environmental or biological substances can build up on the filter and reduce the ability of the filtration unit 12 to function as a filter, which causes a reduced filtering capacity. The filter can be replaced as needed to retain an optimum or desirable filtering capacity.

When included (e.g., in FIG. 2), a sample divider 22 can be any device or system configured to split a sample into two portions or to remove some portion of a sample from the bulk sample. The sample divider 22 can include a wide range of components to facilitate splitting a sample into two or more portions, such as pipettes, valves, fluid conduits and networks, reservoirs, chambers, cutting devices, spatulas, tongs, pumps, and the like. Such a sample divider 22 can be configured to split a solid, paste, gel, liquid or other sample format. The sample divider 22 can be configured to split the filtered sample into two or more separate compositions, one or more of the separate compositions being a test sample and one or more of the separate compositions being a control sample. The sample divider 22 can be operably coupled with the filtration unit 12 to receive a filtered sample, and then operably coupled to the control sample conditioner unit 14 and the analytic unit 16. For example, the sample divider 22 can be operably coupled with the filtration unit 12 by fluid pathways that can move a sample from the filtration unit 12 to the sample divider 22. A pipetting system can also operably couple the filtration unit 12 to the sample divider 22 by being configured to pipette a sample from the filtration unit 12 to the sample divider 22. The sample divider 22 can be similarly associated with the control sample conditioner unit 14.

The sample divider 22 can be configured to split the filtered sample into two compositions at various ratios. The sample splitter can be configured to split the sample into a ratio of 9:1, 4:1, 7:3, 3:2, or 1:1 with respect to the portion sent to the analytic unit 16 compared to the control sample conditioner unit 14. However, other ratios can be used.

The control sample conditioner unit 14 can be configured to remove one or more DNA intercalators from the control sample so as to form a cleansed control sample. This allows a comparison between the filtered environmental sample with and without the DNA intercalators so that the presence or amount of the DNA intercalators can be detected in the analytic unit 16. The control sample conditioner unit 14 can include a hydrophobic component configured to attract and retain hydrophobic DNA intercalators via hydrophobic interaction from the control sample. For example, the hydrophobic component includes octadecylsilyl-based components (e.g., ODS cartridge) and/or hydrocarbon components (e.g., C18) or suitable equivalent that can trap and retain DNA intercalators from the filtered sample. The DNA intercalator can be trapped in the control sample conditioner unit 14 via hydrophobic interaction.

The hydrophobic component that traps the DNA intercalators can be replaceable or replenishable when the DNA intercalator capacity is reduced. Also, the control sample conditioner unit 14 can include a reverse-phase column and associated equipment as the hydrophobic component.

The analytic unit 16 can be configured to receive the test sample and cleansed control sample from the filtration unit 12 (or sample divider 22 in FIG. 2) and control sample conditioner unit 14, respectively. Also, the analytic unit 16 can analyze the test sample and cleansed control sample for the presence of one or more DNA intercalators by running one or more assays. Additionally, the analytic unit 16 can calculate the amount of DNA intercalator in the sample.

The analytic unit can be configured to receive the test sample and conditioned control sample, and to contact the test sample and conditioned control sample with double stranded nucleic acids having a strand linked to an ECA substrate. The analytic unit can then detect an electronic current or change in current that results from the nucleic acids interacting with a DNA intercalator or lack of a DNA intercalator in the test sample and conditioned control sample; and to obtain electronic current from the electronic current passed through the test sample and the cleansed control sample.

The analytic unit 16 can include various types of analytical components or equipment that operate as described herein, and can include one or more different types of analytical components. The analytic unit 16 can include one or more analytical components selected from NMR spectroscopy, UV-vis, FTIR, mass spectrometry. spectrophotometry, colorimetry, chromatography, electrophoresis, crystallography, microscopy, electrochemistry, titration, gravimetry, qualitative analysis, thermal analysis, separation, hybrid techniques (e.g., LC-MS, HPLC-MS, HPLC/ESI-MS, LC-DAD, CE-MS, CE-UV, GC-MS, LC-IR), biochip, chemical arrays, microchip assays (e.g., lab-on-a-chip), and the like as well as combinations of analytical components. The analytical unit can be one piece of equipment or it can be an association of two or more such of such equipment.

In one embodiment, the analytic unit 16 can include a biochip to test for the presence or amount of a particular or various DNA intercalators. A biochip (see: Preliminary evaluation of electrochemical PNA array for detection of single base mismatch mutations, *Lab on a chip* 1: 61-63, 2001; and Microfabricated disposable DNA sensor for detection of hepatitis B virus DNA, *Sensors and Actuators B* 46: 220-225, 1998, which are incorporated herein by specific reference in their entirety) is a collection of miniaturized test sites (e.g., microarrays) arranged on a solid substrate that permits many tests to be performed at the same time in order to achieve higher output and speed. An example of a biochip can be an electronic chemical array (ECA), which includes aspects of biochemistry and semiconductor technologies. Examples of ECAs include without limitation the CoulArray® and Coulochem series manufactured by ESA, and those prepared by Toshiba Corp. The biochips are an assay platform that use, in addition to microarray technology, transduction and signal processing technologies to output the results of sensing experiments. Numerous transduction methods can be employed including electronic potential or change, surface plasmon resonance, fluorescence, and chemiluminescence as well as many others. The particular sensing and transduction techniques chosen depend on factors such as price, sensitivity, and reusability. The actual sensing component (or "chip") is just one piece of a complete analysis system. Transduction is done to translate the actual sensing event (i.e., DNA-intercalator binding) into a format understandable by a computer (e.g., voltage, light intensity, mass, etc.), which then enables additional analysis and processing to produce a final, human-readable output. A "GeneChip" can contain thousands of individual DNA sensors for use in sensing DNA intercalators.

The microarray can include a dense, two-dimensional grid of biosensors. Typically, the sensors are deposited on a flat substrate, which may either be passive (e.g. silicon or glass) or active. An active substrate can include integrated electronics or micromechanical devices that perform or assist signal transduction. Surface chemistry is used to covalently bind the sensor nucleic acids to the substrate medium.

A core principle behind microarrays is hybridization between two DNA strands, one being linked to the substrate. The property of complementary nucleic acid sequences to specifically pair with each other by forming hydrogen bonds between complementary nucleotide base pairs allows for a DNA intercalator to position between the hybridized nucleic acids. The microarrays can use relative quantization in which the intensity of a feature when contacted with a sample is compared to the intensity of the same feature when contacted with the conditioned sample.

A traditional solid-phase microarray can include a collection of orderly microscopic "spots", called features, each with a specific nucleic acid attached to a solid surface, such as glass, plastic or silicon biochip (commonly known gene chip, genome chip, DNA chip or gene array). Thousands of them can be placed in known locations on a single DNA microarray.

Figure 3:
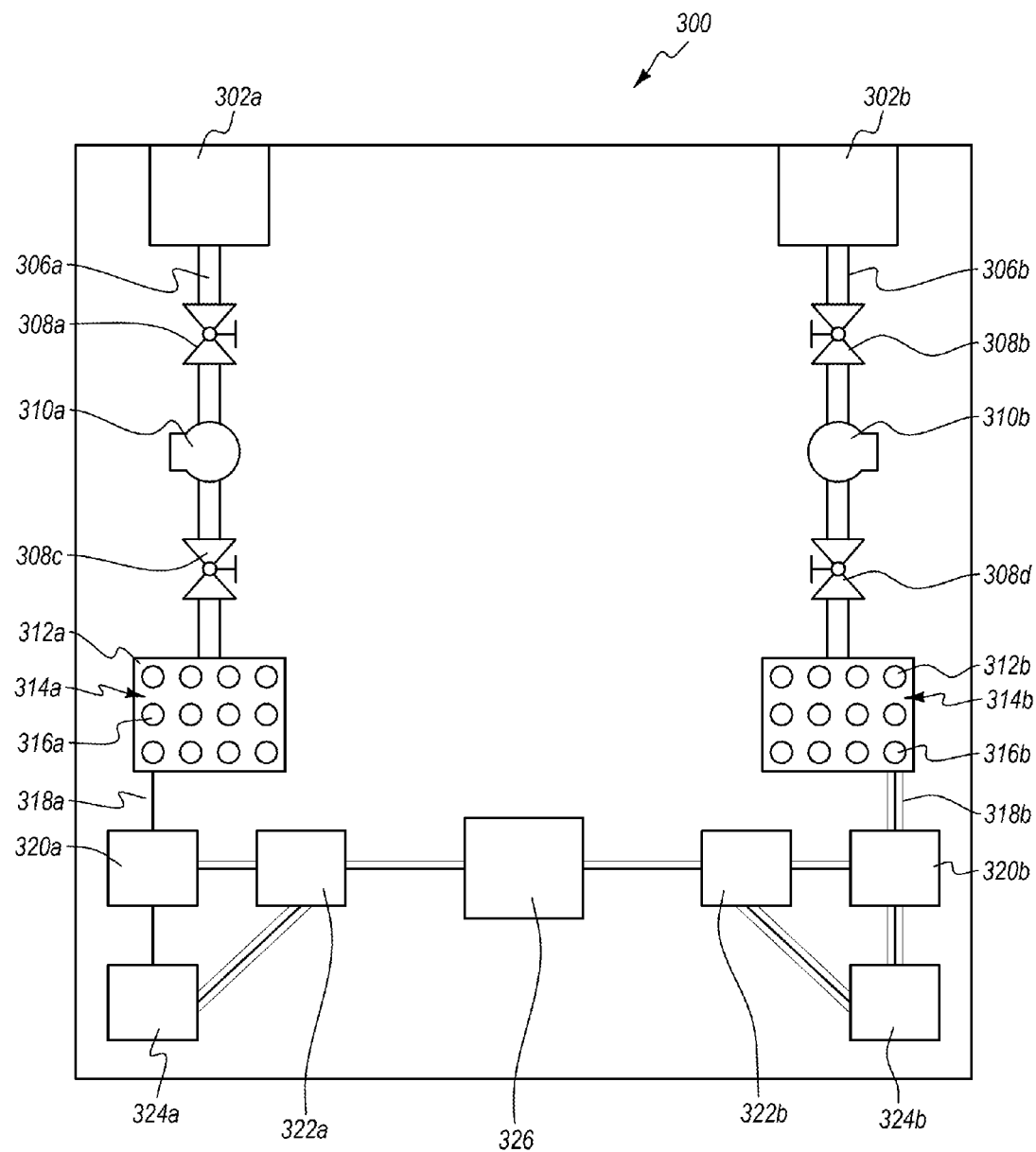
FIG. 3 is an illustrative example of an analytic unit.

FIG. 3A is a schematic diagram of an embodiment of an analytic unit 300. The analytic unit 300 includes an inlet port 302a for the test sample and an inlet port 302b for the conditioned control sample. Each inlet port 302a, 302b is fluidly coupled with a fluid passageway 306a, 306b that includes one or more valves 308a, 308b, 308c, 308d, one or more pumps 310a, 310b that can cooperate to pass the test sample and conditioned control sample to an electronic chemical array (ECA) chip 312a, 312b for analysis. The ECA chips 312a, 312b, can include an array 314a, 314b, of analytic modules 316a, 316b. Each analytic module 316a, 316b is associated with one or more electronic pathways 318a, 318b that can pass an electronic current to one or more electronic detectors 320a, 320b. The electronic detectors 320a, 320b can be configured detect and/or determine a change in current with respect to electrodes (not shown) of the analytic modules 316a, 316b. The electronic detectors 320a, 320b can be associated with data communication modules 322a, 322b that can be configured to transmit electronic data from the analytic modules 316a, 316b to a remote or onboard data processing unit 324a, 324b. The data communication modules 322a, 322b can also receive operation instruction data from the remote or onboard data processing unit 324a, 324b and pass the data to an analytic unit controller 326, which can be configured as a computing system or microprocessor and associated computing components. The analytic unit controller 326 can be operably coupled with the one or more inlet ports 302a, 302b, valves 308a, 308b, 308c, 308d, pumps 310a, 310b, and ECA chips 312a, 312b so as to provide operation instruction data thereto.

In one embodiment, the biochip can include an electronic chemical array (ECA) chip. The electronic chemical array can include a polynucleotide coupled with a substrate and a complementary polynucleotide thereof that hybridizes with the polynucleotide coupled with the substrate. The polynucleotides can be of any size ranging from about 8 nucleotides to about 100 or more nucleotides, about 10 to about 75 nucleotides, about 20 to about 50 nucleotides or about 25 to about 30 nucleotides. The polynucleotide coupled to the substrate can have any sequence of nucleotides, and the complementary polynucleotide can have a sequence that hybridizes to the polynucleotide coupled to the substrate.

The presence of DNA intercalators can then be identified by a difference in the electronic current of the ECA chip between the conditioned control sample (e.g., having DNA intercalators removed) and the sample suspected of having the DNA intercalators (e.g., filtered or test sample). Also, the analytic unit 16 can be configured to contact the test sample and conditioned control sample with double stranded nucleic acids having a strand linked to an electronic chemical array (ECA) reaction surface. The analytic unit 16 can be configured to detect or measure an electronic current or change in electronic current through the test sample and conditioned control sample. The analytic unit 16 can include detection electrodes (e.g., detection electrode, reference electrode, and counter electrode) that can obtain electronic data (e.g., voltage, resistance, current, amplitude, or changes thereof) from the electronic current detected or measured from the test sample and the conditioned control sample.

The electrodes can operate with the systems and methods described herein by performing a linear sweep voltammetry (LSV) (see, Preliminary evaluation of electrochemical PNA array for detection of single base mismatch mutations, *Lab on a chip* 1: 61-63, 2001). LSV is a voltammetric method where the current at the working electrode is measured while the potential between the working electrode and a reference electrode is swept linearly in time. By LSV, oxidation or reduction of species is registered as a peak or trough in the current signal at the potential at which the species begins to be oxidized or reduced. As such, a change in current as detected by the working electrode can be used as the electronic data.

In another embodiment, the analytic unit 16 can optionally include one or more of: a port fluidly coupled with the sample divider 22 so as to be configured to receive the test sample; a port fluidly coupled with the control sample conditioner unit 14 so as to be configured to receive the conditioned control sample; one or more sample chambers configured to receive one or more samples; one or more fluid pathways configured to deliver the test sample and conditioned control sample to the one or more sample chambers; an integrated or removable ECA; a working electrode, counter electrode, and/or reference electrode; a nucleic acid strand coupled with one of the electrodes; a complementary nucleic acid strand hybridizable with the electrode-coupled nucleic acid; electronic components configured to cause an electronic current to be passed through the electrode-coupled nucleic acid; voltammetry electronic components; electronic components configured to obtain the electronic current; a transmitter to transmit electronic current to the data processing unit; or a receiver to receive instructions from the data processing unit.

Figure 4:
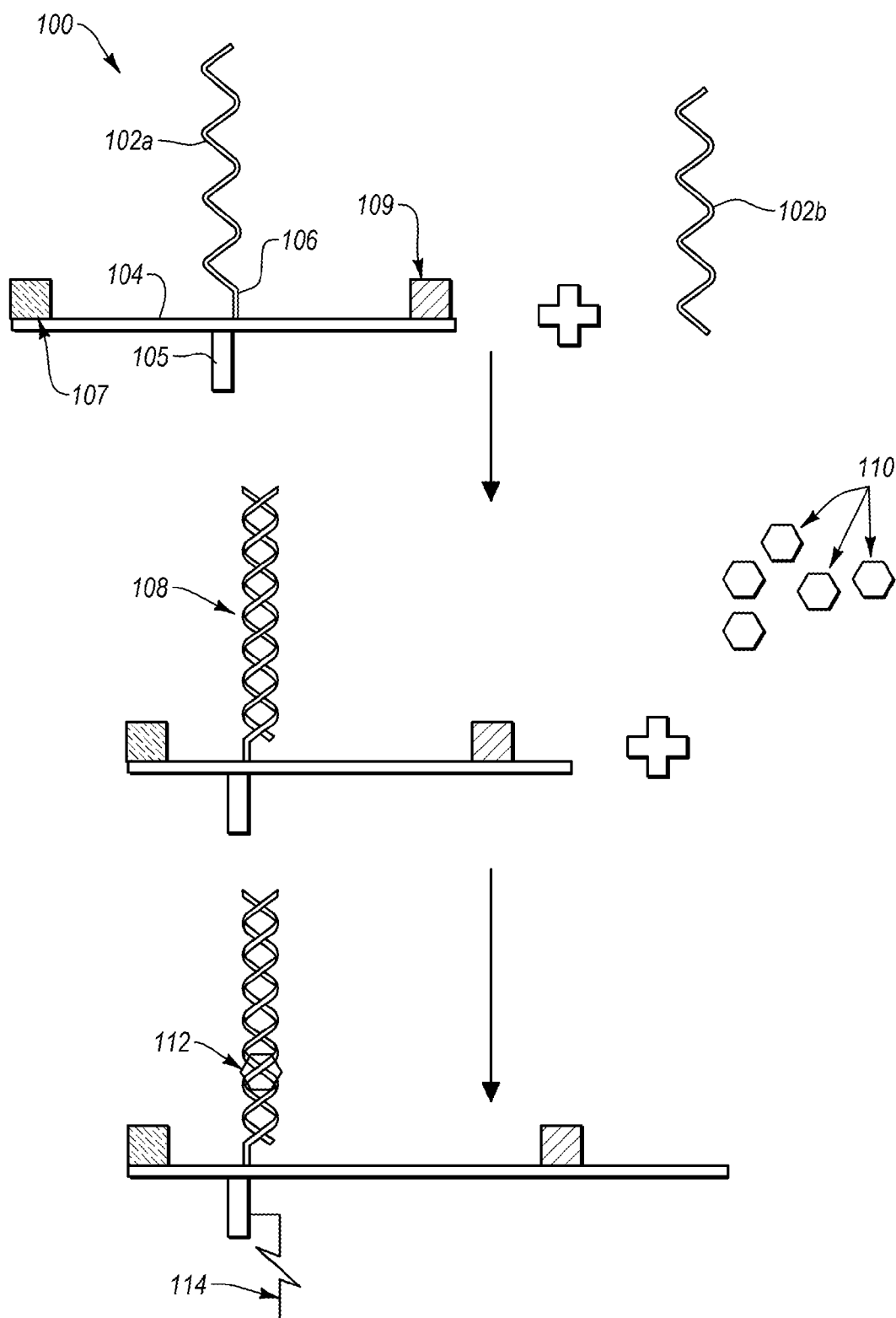
FIG. 4 is an illustrative example of a method of performing DNA intercalator testing with the system described herein.

FIG. 4 schematically shows a process 100 that can be performed with the ECA chip of the analytic unit to determine whether or not a DNA intercalator is present in a sample or the amount thereof. The chip can include a nucleic acid 102a (e.g., DNA) covalently linked with a substrate 104. The substrate 104 can be associated with a working electrode 105 (e.g., copper, titanium, silver, gold or other electrode materials) such that the working electrode 105 can receive an electronic current from the nucleic acid 102a through the association of the substrate 104 and working electrode. In one aspect, the substrate 104 can be the working electrode 105. The nucleic acid 102a can be arranged with a reference electrode 107 and a counter electrode 109 so as to form a circuit capable of having an electronic current. The nucleic acid 102a can be linked to the substrate 104 by a covalent bond or a linker 106 or the like. A complementary nucleic acid 102b can be hybridized with the nucleic acid 102a to form a duplex 108. The complementary nucleic acid 102b can be combined with the nucleic acid 102a before, during, or after combining a sample with the nucleic acid 102a by being introduced to the ECA chip. Before, during, or after forming the duplex 108, the sample containing one or more potential DNA intercalators 110 can be introduced to the ECA chip having the duplex 108. The DNA intercalator(s) 110 of the sample can then intercalate with the duplex 108 as shown by the intercalation 112. Upon the DNA intercalator 110 intercalating with the duplex 108, an electronic current 114 generated the duplex 108 can be identified or measured. The electronic current 114 can be generated by the intercalation event, which arises from the formation of a kind of charge-transfer complex upon intercalation.

The electronic current 114 can be derived from a redox reaction between the DNA intercalator 110 and the duplex 108. The electronic current 114 can depend on the amount of DNA intercalator 110 present in the sample. Each type of DNA intercalator 110 can have a unique electric potential. The amount of electronic current 114 or change in current can vary in a positively correlated manner with the DNA intercalator 110.

The amount of nucleic acid 102a bound to the substrate 104 (e.g., optionally conductive material operating as a working electrode) at a defined location can vary widely. For example, the amount can be on the order of about $10^{-10}$ to $10^{-10}$; however, other amounts can be used. The nucleic acid 102a can also be longer than an 8 mer, such as greater than a 12 mer, greater than a 20 mer, or more. An example can be about 20 to about a 25 mer nucleic acid. The nucleic acid 102a can be present in range from $1\times10^{-18}$ to $1\times10^{-10}$, $1\times10^{-16}$ to $1\times10^{-12}$, or $1\times10^{-14}$ to $1\times10^{-13}$ moles.

Figure 5:
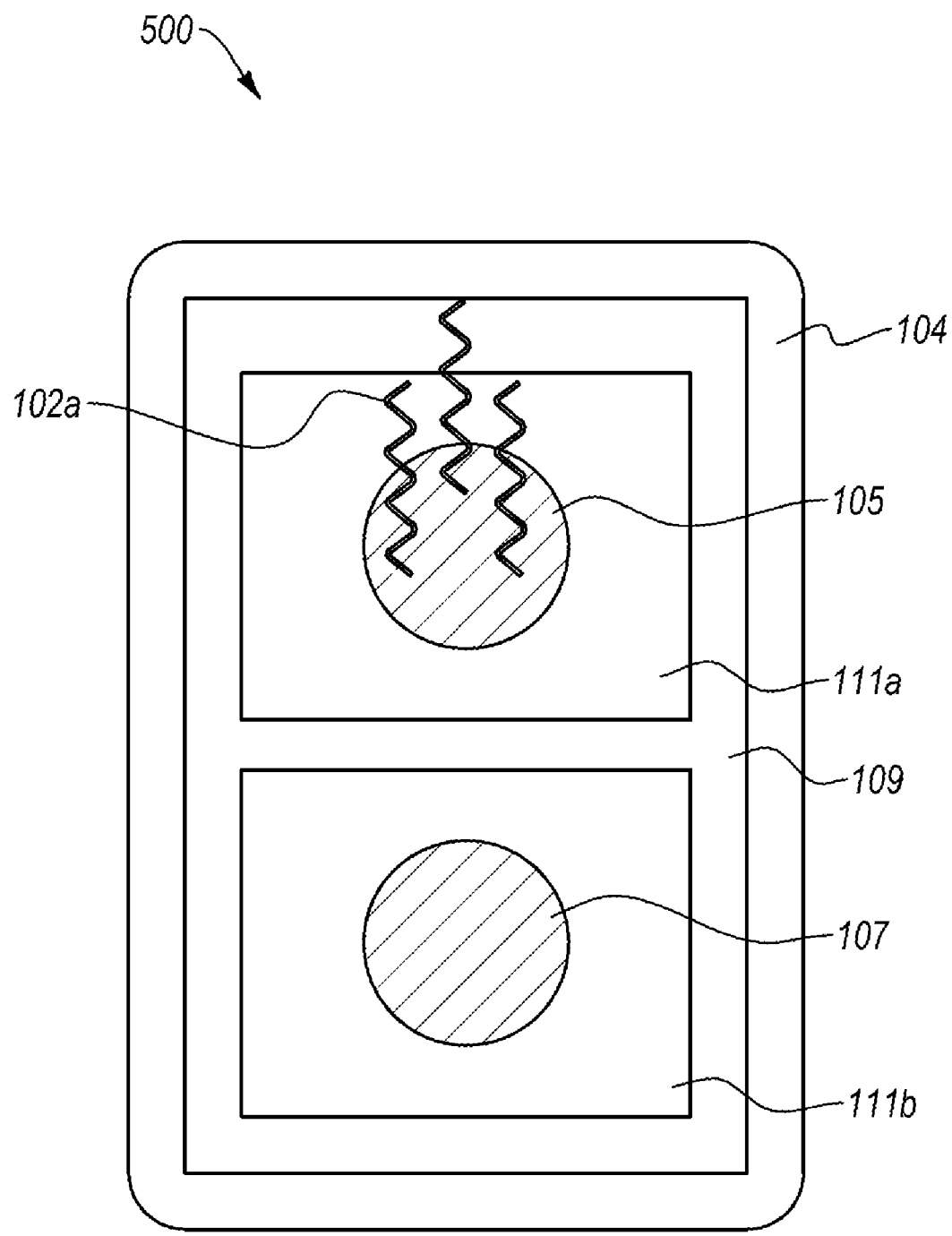
FIG. 5 is an illustrative example of an electrochemical array (ECA) analytic module.

FIG. 5 illustrates another embodiment of an ECA 500 with the arrangement of the substrate 104 and the electrodes 105 (working), 107 (reference), 109 (counter). As shown, the substrate 104 has a counter electrode 109 located directly on its surface. The counter electrode 109 has one or two insulators 111a, 111b located directly on the surface of the counter electrode 109. A working electrode 105 is located directly on the surface of an insulator 111a in a manner such that the working electrode 105 is spaced apart and not touching the counter electrode 109 and/or the reference electrode 107. A reference electrode 107 is located directly on the surface of an insulator 111b in a manner such that the reference electrode 107 is spaced apart from the counter electrode 109 and/or working electrode 105. The working electrode 105 can have the nucleic acid 102a bound directly thereto.

Figures 6A, 6B:
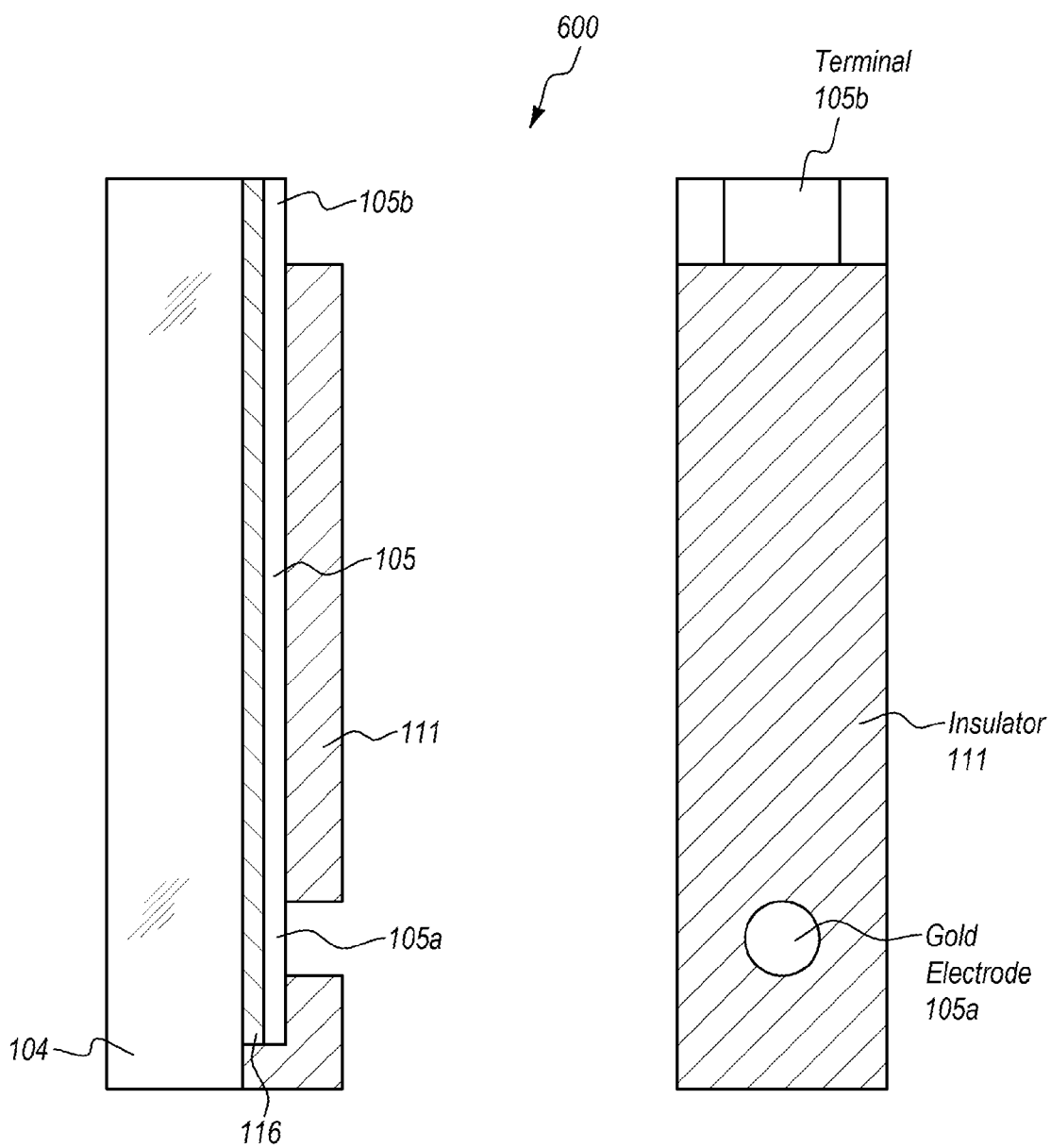
FIGS. 6A-6B are illustrative examples of an electrochemical array (ECA) analytic module.

FIGS. 6A-6B illustrate an embodiment of an ECA 600 having a substrate 104 having a working electrode 105. The substrate 104 is disposable and configured to be received into the analytic unit 16, where the analytic unit includes the reference and/or counter electrodes (not shown) in predetermined orientations for conducting current analysis and current change detection as described herein. As shown, the substrate 104 is glass and approximately 30 mm long, 1.5 mm wide, and 1 mm thick. A layer of titanium 116 is sputtered onto the glass substrate 104 and about 500 angstroms to about 50 nm thick. A layer of gold for the working electrode 105 is sputtered onto the titanium layer 116 and is about 5000 angstroms to about 200 nm thick. An insulator 111 is formed onto the gold working electrode 105 so as to form a gold electrode spot 105a for receiving the nucleic acid and form a terminal 105b that can be electronically coupled with the analytic unit 16 when received therein.

Figure 7A:
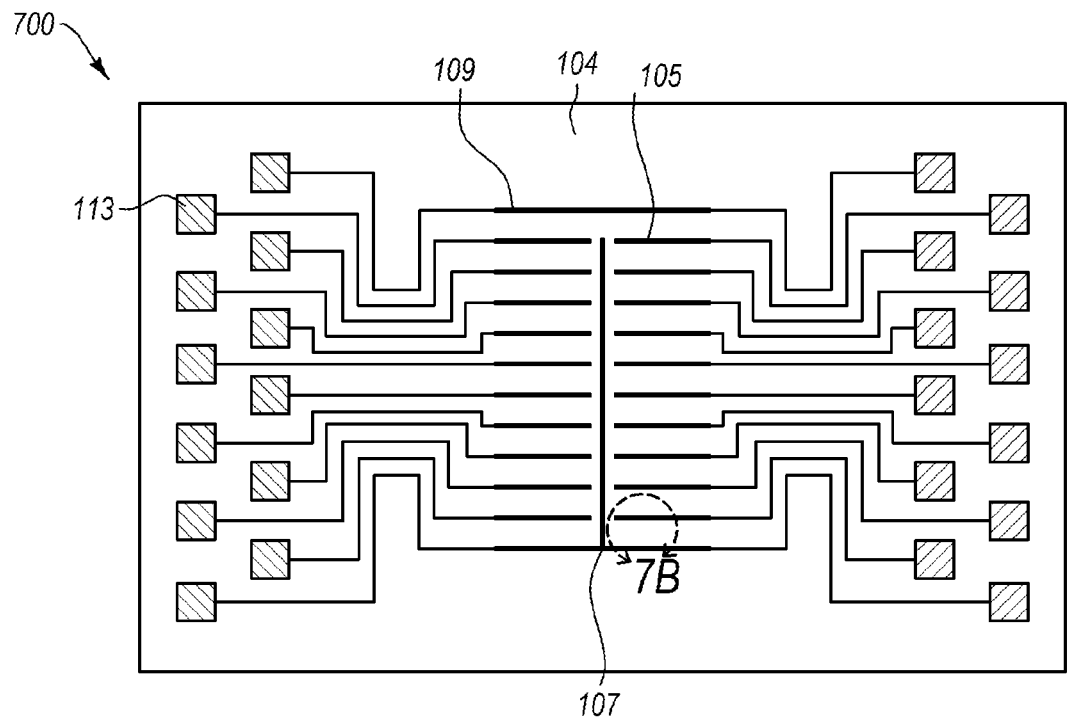
FIGS. 7A-7B are illustrative examples of an electrochemical array (ECA) analytic module.
Figure 7B:
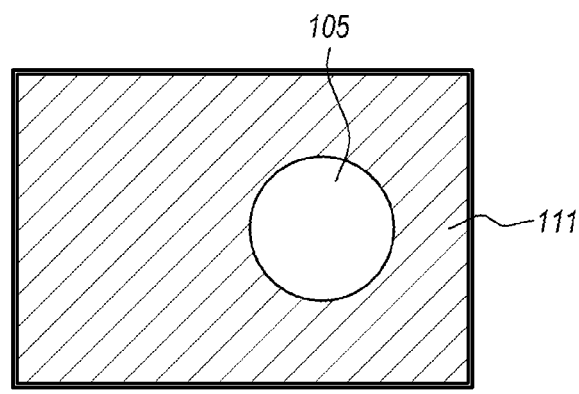

FIGS. 7A-7B an embodiment of an ECA 700 having a substrate 104 configured to be received into the analytic unit 16. As shown, the substrate 104 includes a working electrode 105 located on an insulator 111 and in proximity to a counter electrode 109 and a reference electrode 107. The working electrode 105, reference electrode 107, and counter electrode 109 are each electronically coupled to a connecting pad 113. The connecting pad 113 is configured to be electronically coupled with the analytic unit 16 when the ECA 700 is received therein.

The amount of a DNA intercalator 110 that can be detected can range through parts per trillion (ppt), parts per billion (ppb), parts per million (ppm), nanomolar (nM), micromolar (mM) and the like. This can allow for the degree of detection sensitivity to DNA intercalators.

For example, if a DNA intercalator 110 is present in the analytical sample, it will enter a gap between the nucleic acid 102a and its complement 102b, thereby forming a charge-transfer complex which can generate or modulate the electric current being detected. That is, the intercalation event generates or modulates the current 114. For example, in one instance there will be an inherent current from the duplexed polynucleotide coupled to the substrate due to the electrode system, and the DNA intercalator changes this current to modulate the electronic data. In another example, there may not be an inherent current arising from the arrangement of the duplexed polynucleotide and electrode arrangement, and the DNA intercalator generates a current by intercalating with the DNA. The value of the current 114, which is derived from the redox of the DNA intercalator 110, can depend on the amount of DNA intercalator 110 present in the sample for the specific electric potential of the DNA intercalator unique to a target DNA intercalator. Different DNA intercalators can have different electric potentials. The amount of the current can vary in an amount that correlates to a particular DNA intercalator. In one instance for a ferrocene derivative, the electric potential or varied current can be about 619 mV.

The nucleic acid-linked electrode can be the working electrode. A counter electrode and optionally a reference electrode can be included. The counter electrode can be platinum or other similar material. The reference electrode can be silver/silver-chloride in a suitable buffer-containing electrolyte. The complementary nucleic acid 102b can be included at any time before the sample is contacted to the nucleic acid.

In one example, an equimolar amount of DNA (or more) that has a complementary sequence with the DNA linked to the chip can be added to the chip so as to be configured to hybridize therewith.

The analytical unit 16 can optionally include a port (not shown) coupled (e.g., fluidly coupled when sample is a liquid) with the sample divider 22 so as to be configured to receive the test sample, and/or a port coupled with the control sample conditioner unit 14 so as to be configured to receive the conditioned control sample. The ports can be any type of sample receiving component.

The analytical unit 16 can optionally include one or more sample chambers (not shown) configured to receive one or more samples. The chambers can be any type of reaction or assay chamber for analyzing the sample and/or the conditioned sample.

The analytic unit 16 can optionally include one or more pathways (not shown) (e.g., fluid pathway, mechanical mover, etc.) configured to deliver the test sample and conditioned control sample to the one or more sample chambers.

In still another embodiment, the analytic unit 16 can include an integrated or removable biochip or ECA reaction component. A biochip or ECA reaction component can include a working electrode, counter electrode, and/or reference electrode so that electronic differences between the sample and conditioned sample can be assessed. The biochip or ECA can include a nucleic acid strand operably coupled with one of the electrodes, such that electronic data (e.g., electronic current) related to a DNA intercalator 110 interacting with the nucleic acid 102a can be detected and obtained. The biochip or ECA can also include a complementary nucleic acid strand hybridizable or hybridized with the electrode-coupled nucleic acid such that a DNA intercalator 110 can be intercalated between the nucleic acid 102a and the complementary nucleic acid 102b to generate or change the electronic current 114.

In still another embodiment, the analytical unit 16 can include voltammetry electronic components that can perform votammetry methods. Voltammetry is a category of electroanalytical methods used in analytical chemistry and various industrial processes. In voltammetry, information about an analyte (e.g., DNA intercalator) is obtained by measuring the current as the potential is varied. Voltammetry experiments can investigate the half cell reactivity of an analyte. Most experiments control the potential (volts) of an electrode in contact with the analyte while measuring the resulting current (amperes). Conducting such a votammetry experiment involves at least two electrodes, i.e., a working electrode and a reference electrode. The working electrode, which makes contact with the analyte, applies the desired potential in a controlled way and facilitates the transfer of electrons to and from the analyte. A counter electrode acts as the other half of the cell. This counter electrode can have a known potential with which to gauge the potential of the working electrode, furthermore it can balance the electrons added or removed by the working electrode. The role of supplying electrons and referencing potential can be divided between two separate electrodes.

A three electrode detection system can include the working electrode, reference electrode, and counter electrode. The reference electrode can be a half cell with a known reduction potential. Its only role is to act as reference in measuring and controlling the working electrodes potential. The auxiliary electrode passes the current needed to balance the current observed at the working electrode. To achieve this current, the auxiliary will often swing to extreme potentials at the edges of the solvent window, where it oxidizes or reduces the solvent or supporting electrolyte. These electrodes, the working, reference, and auxiliary make up the modern three electrode system. For example, a cyclic voltammogram can be generated.

The analytic unit 16 can include a transmitter (not shown) to transmit electronic data 114 to the data processing unit 18. Also, the analytic unit 16 can include a receiver (not shown) to receive instructions from the data processing unit 18. A transceiver can be included in place of a separate transmitter and receiver.

The data processing unit 18 can be operably coupled with the analytic unit 16 and configured to compare and determine a difference between the electronic current 114 from the test sample and the conditioned control sample. The difference in electronic current 114 can provide an indication of whether or not a DNA intercalator 110 is present in the sample. The processing unit 18 can be any type of computing system with hardware and software that can be used to receive data from the analytic unit 16 and process the data in order to determine the presence or amount of the DNA intercalator 110 in the environmental sample. The presence or levels of one or more DNA intercalators 110 can be identified in the environmental sample by comparing the current 114 or other electronic data of the filtered sample with various standards or with the conditioned sample (e.g. DNA intercalators removed). The standards can be certain electric potential or electronic data, which is unique to a target DNA intercalator 110.

In general, LSV data are affected by measurement conditions. As such, the values obtained by the same analyte during an LSV procedure, such its peak potential and current, are varied depending upon the condition used. Therefore, the DNA intercalators that are to be detected with the system and methods described herein can be pre-tested in order to identify their electrochemical characteristics including dose responses under conditions of the systems and methods used in the analysis.

For example, the electronic data related to the difference between the sample and control can be current data. When the difference is below a "selected value" (e.g., 20 nA) it is considered that the target DNA intercalator 110 is either not present or present in a minimal or low risk amount, when the difference is between selected values (e.g., between 20 nA and 40 nA) it is considered that the target DNA intercalator 110 is present and at an intermediate or medium risk, and when the difference is greater than a selected value (e.g., greater than 40 nA) it is considered that the target DNA intercalator 110 is present at a significant amount that is considered a high risk. The "selected value" is only a rough estimate and determined by pre-testing the DNA intercalator to be detected. The "selected value" is arbitrary and dependent on the type of DNA intercalator, and the configuration of the detection system as well as on the method used for the detection procedure. The "selected values" described herein are relevant to Hoechst 33258 (a DNA intercalator) in the water sample by LSV using the system and methods described herein.

Also, the data processing unit 18 can include hardware and/or software configured to operate components of the system. With such hardware and/or software, the data processing unit 18 can be operably coupled with the filtration unit 12, sample divider 22, control sample conditioner unit 14 and the analytic unit 26.

Figure 8A:
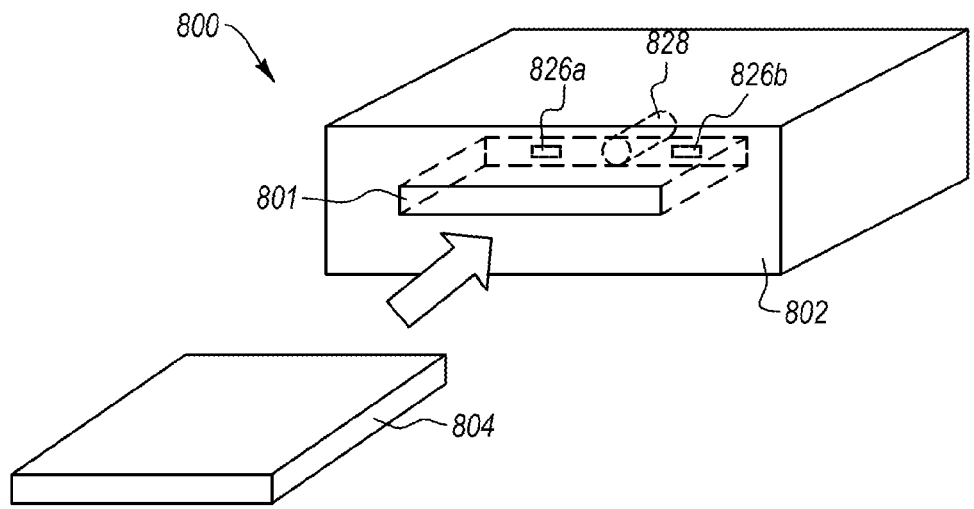
FIGS. 8A-8B are illustrative examples of a portable DNA intercalator testing system.
Figure 8B:
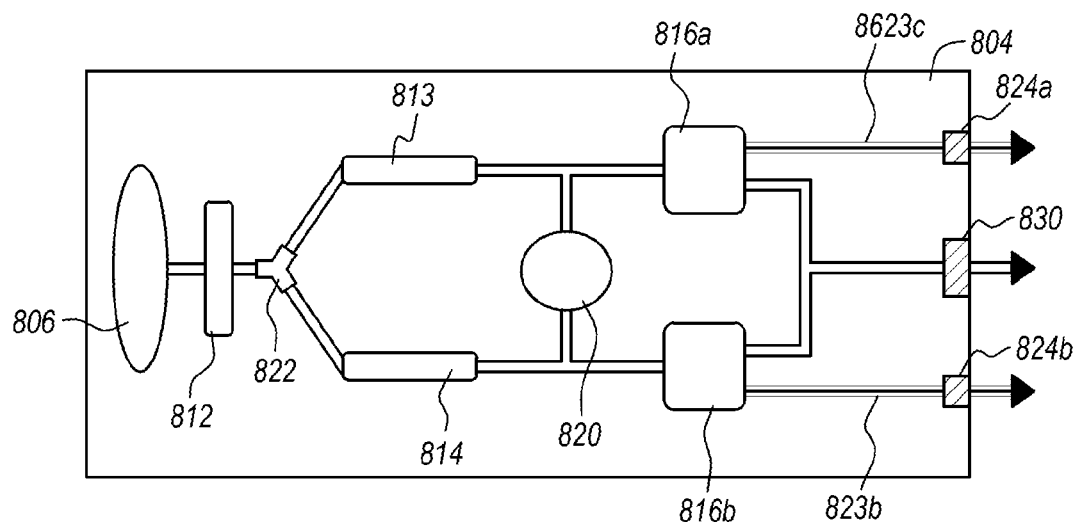

FIGS. 8A-8B illustrate another embodiment of a DNA intercalation detection system 800 that includes a main housing 802 with a port 801 configured to receive a removable cartridge 804. The port 801 of the main housing 802 can include a first connector 810a and a second connector 810b which are configured to be electronically coupled with electronic connectors 824a, 814b of the removable cartridge 804. The port 801 of the main housing 802 can also include a suction pump 828 configured to be fluidly coupled with a fluid outlet 830 of the removable cartridge 804. The main housing 802 may optionally include an onboard data processing unit (not shown) or can be operably coupled with an external data processing unit 18.

The removable cartridge 804 can include a sample port 806 fluidly coupled with a filtration unit 812 that is also fluidly coupled with a sample divider 822 that is configured to split a filtered sample. The sample divider 822 is fluidly coupled with a test sample conditioner unit 813 and a control sample conditioner unit 814. The test sample conditioner unit 813 is fluidly coupled to a first analytic unit 816a, and the control sample conditioner unit 814 is fluidly coupled to a second analytic unit 816b. An oligonucleotide reservoir 820 is also fluidly coupled with the first analytic unit 816a and the second analytic unit 816b. The oligonucleotide reservoir 820 is configured to include the antisense nucleic acid 102b that hybridizes with the substrate-bound nucleic acid 102a. The oligonucleotide reservoir 820 can also include a medium, such as a liquid buffer, for moving the oligonucleotide 102b into the analytic units 816a, 816b. The analytic units 816a, 816b are each electronically coupled through electronic pathways 823a, 623b to electronic connectors 824a, 824b that can be electronically coupled with the first connector 810a and second connector 810b of the main housing 812. The removable cartridge 804 can also include a fluid outlet 830 that is fluidly coupled with the first analytic unit 816a and the second analytic unit 816b, and is configured to be fluidly coupled with the suction pump 828 of the main housing 802 when the removable cartridge 804 is received into the port 802 of the main housing 802.

The filtration unit 812, sample divider 822, control sample conditioner unit 814, and the analytic units 816a, 816b can be configured as described herein. The sample port 806 can be configured as any type of fluid sample receiving component, such as a reservoir or container. The test sample conditioner unit 813 can be configured similarly as the control sample conditioner unit 814 except that it does not include a material (ODS) that binds with a hydrophobic DNA intercalator; instead the test sample conditioner unit 813 can include an inert silica gel or other inert medium that does not react or interact with a hydrophobic DNA intercalator.

The removable cartridge 804 can be configured to be disposable. Also, the removable cartridge 804 can be configured as a microfluidic device where the fluid pathways are microchannels and the components are microcomponents.

The system can include one or more user interfaces (not shown), which include a user input interface and an output interface. Such user interfaces can include graphical displays, printer, sound speakers, microphone, keyboards, mouse, light pens, touch screens, buttons, knobs, levers, switches, lights, and the like. For example, each components of the system can include separate user interfaces, or a central user interface can be configured to control some or all of the components.

Embodiments of the system or data processing unit 18 may include or utilize a special purpose or general-purpose computer including computer hardware, as discussed in greater detail below. Embodiments within the scope of the system and data processing unit 18 also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media including recordable-type storage media. Computer-readable media that carry computer-executable instructions are transmission media. Thus, by way of example, and not limitation, embodiments of the system can comprise at least two distinctly different kinds of computer-readable media: physical storage media and transmission media.

Physical storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

The system or data processing unit 18 can be linked to a network so that the data can be transmitted remotely via wire, optical, wireless or the like. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry or transport desired program code means in the form of computer-executable instructions or data structures and which can be accessed by a general purpose or special purpose computer. Combinations of the above should also be included within the scope of computer-readable media.

However, it should be understood, that upon reaching various computer system components, program code means in the form of computer-executable instructions or data structures can be transferred automatically from transmission media to physical storage media. For example, computer-executable instructions or data structures received over a network or data link can be buffered in RAM within a network interface card, and then eventually transferred to computer system RAM and/or to less volatile physical storage media at a computer system. Thus, it should be understood that physical storage media can be included in computer system components that also (or even primarily) utilize transmission media.

The system or data processing unit 18 can include a storage medium having computer-executable instructions for performing the analytical protocols and/or data processing as described herein. Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the data acquisition or data communication may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The data processing or communication may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

One skilled in the art will appreciate that for processes and methods disclosed herein the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an"

should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method for detecting a DNA intercalator in an environmental sample, the method comprising:
    obtaining the environmental sample from an environment, the environmental sample having one or more DNA intercalators or being devoid of the one or more DNA intercalators;
    removing a portion of the environmental sample to obtain a control sample;
    conditioning the control sample such that the one or more DNA intercalators are removed therefrom, if present in the environmental sample, to form a conditioned control sample;
    contacting the environmental sample with double stranded nucleic acids having a strand linked to an electronic chemical array, wherein the environmental sample is unfiltered;
    contacting the conditioned control sample with double stranded nucleic acids having a strand linked to an electronic chemical array;
    detecting an electronic current generated by the environmental sample and an electronic current generated by the conditioned control sample; and
    determining a difference between the electronic current of the environmental sample and the conditioned control sample, said difference providing an indication of whether or not a DNA intercalator is present in the environmental sample.

2. The method of claim 1, further comprising collecting the environmental sample from a location and performing the method at the location.

3. The method of claim 1, further comprising filtering the control sample, wherein filtering comprises removing biological materials without removing the DNA intercalators therein if present.

4. The method of claim 1, further comprising contacting one or more portions of the control sample to a DNA intercalator trap member adapted to attract and retain DNA intercalators therefrom.

5. The method of claim 1, comprising measuring the electronic currents of the environmental sample and conditioned control sample.

6. The method of claim 1, comprising hybridizing a nucleic acid strand coupled to the electronic chemical array with its complementary nucleic acid.

7. The method of claim 1, comprising conducting a voltammetry protocol.

8. The method of claim 1, further comprising processing electronic data obtained from the environmental sample and conditioned control sample in order to determine a difference between the electronic data from the environmental sample and the conditioned control sample.

9. The method of claim 1, further comprising determining an amount or health risk of a DNA intercalator.

10. The method of claim 9, wherein the determining the health risk is performed by identifying the difference between the electronic current of the environmental sample with the electronic current of the conditioned control sample.

* * * * *